United States Patent [19]

Chang et al.

[11] 4,076,761
[45] * Feb. 28, 1978

[54] PROCESS FOR THE MANUFACTURE OF GASOLINE

[75] Inventors: Clarence D. Chang, Princeton, N.J.; Anthony J. Silvestri, Morrisville, Pa.

[73] Assignee: Mobil Oil Corporation, New York, N.Y.

[*] Notice: The portion of the term of this patent subsequent to Jul. 8, 1992, has been disclaimed.

[21] Appl. No.: 529,779

[22] Filed: Dec. 5, 1974

Related U.S. Application Data

[63] Continuation of Ser. No. 387,220, Aug. 9, 1973, abandoned.

[51] Int. Cl.² .................. C07C 15/00; C10G 1/06
[52] U.S. Cl. ............................ 260/668 R; 260/449.5
[58] Field of Search ............ 260/668 R, 682, 676, 260/671, 677, 672 T, 668 A, 449.5, 668; 208/135, 141, 118, 120

[56] References Cited

U.S. PATENT DOCUMENTS

| | | | |
|---|---|---|---|
| 3,728,408 | 4/1973 | Tobias | 260/668 C |
| 3,856,873 | 12/1974 | Burress | 260/672 T |
| 3,894,105 | 7/1975 | Chang et al. | 260/668 R |

FOREIGN PATENT DOCUMENTS

| | | | |
|---|---|---|---|
| 1,164,407 | 9/1969 | United Kingdom | 260/449.5 |

Primary Examiner—D. Horwitz
Attorney, Agent, or Firm—Charles A. Huggett; Michael G. Gilman

[57] ABSTRACT

Synthesis gas comprising a mixture of carbon monoxide and hydrogen is derived from fossil fuels and catalytically converted in a first reaction zone to a mixture of methanol and dimethyl ether which in turn is converted in a separate reaction zone in contact with a crystalline aluminosilicate zeolite catalyst having a silica to alumina ratio of at least about 12 and a constraint index of about 1 to 12, and preferably a crystal density in the hydrogen form of not substantially below about 1.6 grams per cubic centimeter to a product which is resolved into a high octane gasoline fraction, a light hydrocarbon gas fraction which may be liquefied and a hydrogen-rich gaseous by-product which is recycled to the conversion of fossil fuels to synthesis gas or may be otherwise used.

4 Claims, 1 Drawing Figure

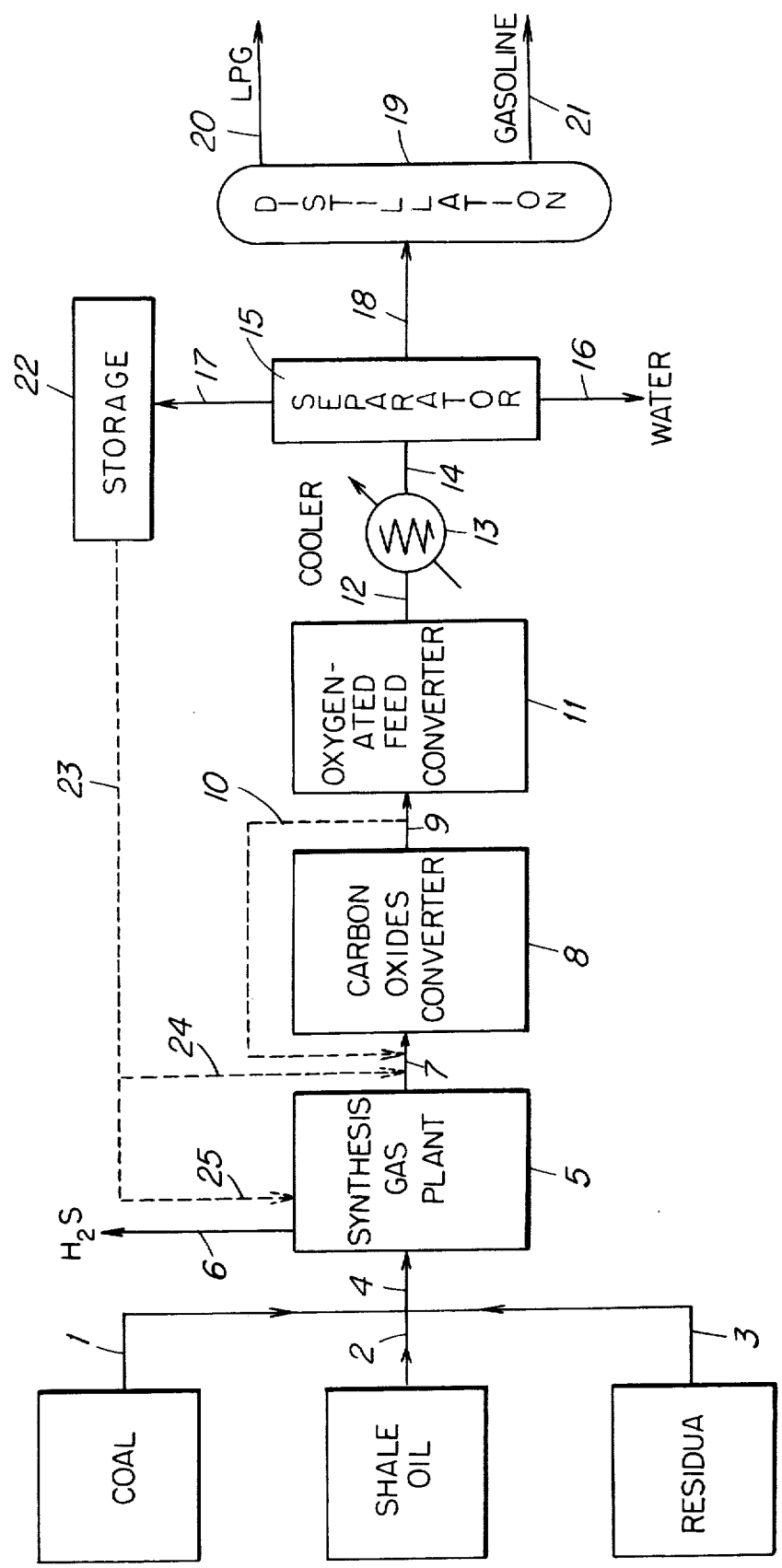

PROCESS FOR THE MANUFACTURE OF GASOLINE

This is a continuation of Application Ser. No. 387,200, filed Aug. 9, 1973 now abandoned.

BACKGROUND OF THE INVENTION

This invention is concerned with a process for converting coal and other solid, highly viscous liquid, or gaseous fossil fuels to liquid petroleum products, particularly hydrocarbon fuels. It more especially is concerned with converting such materials to high quality gasoline.

The increasing demand for high octane gasoline has been met, until now, by advanced petroleum refining technology. The two processes which have made it possible to satisfy the demand are: catalytic cracking, which serves to increase the fraction of crude petroleum which can be brought into the gasoline boiling range; and catalytic reforming, which serves to upgrade the octane number of low grade gasoline. Obviously, the cracking process increases the gasoline yield at the expense of the heavier fuel fractions, such as No. 2 fuel oil, which also is subject to growing demand. The increasing cost of petroleum, together with the foreseen increase in demand for gasoline and other petroleum fractions, makes it necessary to seek other fuel sources from which to make high quality gasoline.

Coal, for example, is an obvious alternative raw material, since there are abundant deposits of this fuel. Gasoline has been made from coal by gasification and conversion of the gases to gasoline by the Fischer-Tropsch process. However, this process, not presently used in this country, produces an extremely poor quality of gasoline, with an octane number of about 55, which cannot be efficiently upgraded by the known catalytic reforming processes because it consists predominantly of straight-chain aliphatic hydrocarbons.

Processes for the conversion of coal and other hydrocarbons to a gaseous mixture consisting essentially of hydrogen and carbon monoxide, or of hydrogen and carbon dioxide, or of hydrogen and carbon monoxide and carbon dioxide, are well known. Such a gaseous mixture hereinafter will be referred to simply as synthesis gas.

Although various processes may be employed for the gasification, those of major interest for the present invention depend either on the partial combustion of the fuel with oxygen, or on the high temperature reaction of the fuel with steam, or on a combination of these two reactions. In one known variant, for example, coal may be completely gasified by first coking, and then subjecting the coke to a cyclic blue water gas process in which the coke bed is alternately blasted with air to increase the bed temperature and then reacted with steam to produce the synthesis gas. The gases generated by the coking step may be used as fuel or steam-reformed to additional synthesis gas. In another process coal or coke may be reacted with highly superheated steam or with oxygen and steam to produce synthesis gas. Regardless of the process variants chosen, oxygen rather than air is often used in the chemical step in which the fuel is converted to synthesis gas since the use of air would result in a gas that contained excessive amounts of inert nitrogen.

An excellent summary of the art of gas manufacture, including synthesis gas, from solid and liquid fuels, is given in Encyclopedia of Chemical Technology, Edited by Kird-Othmer, Second Edition, Volume 10, pages 353–433, (1966), Interscience Publishers, New York, N.Y., the contents of which are herein incorporated by reference. The techniques for gasification of coal or other solid, viscous or gaseous fuel are not considered to be per se inventive here.

It is known that raw synthesis gas contains one or more of the following impurities; sulfur compounds, nitrogen compounds, particulate matter and condensibles. The art of removing these contaminants is known, and is described in the above reference and elsewhere. Particular attention is called to the sulfur compounds. It is desirable to reduce this contaminant below a prescribed level for ecological purposes.

Purified synthesis gas ordinarily contains a volume ratio of hydrogen to carbon monoxide plus carbon dioxide of from as little as about 0.10 to as much as 1.1, depending on the particular fuel and process used; in most instances, the composition has a volume ratio from about 0.30 to about 0.65. It is well known that this ratio may be increased by the catalytic carbon monoxide shift reaction described by the equation:

$$CO + H_2O \rightleftarrows CO_2 + H_2$$

with subsequent removal of at least part of the produced $CO_2$ to bring said volume ratio into a desired high range. The catalytic carbon monoxide shift reaction is commonly conducted with a chromia promoted iron oxide catalyst at a flow rate of about 300–1000 standard cubic feet of gas per cubic foot of catalyst bed per hours, and at sufficiently elevated temperature to allow quasi-equilibration, which is usually about 700° F.

Synthesis gas will undergo conversion to form reduction products of carbon monoxide, such as alcohols, at from about 300° F to about 850° F, under from about 1 to 1000 atmospheres pressure, over a fairly wide variety of catalysts. The types of catalyst that induce conversion include ZnO, Fe, Co, Ni, Ru, $ThO_2$, Rh and Os.

Catalysts based on ZnO are particularly suited for the production of methanol and dimethyl ether. Catalysts based on Fe, Co, and Ni, and especially Fe, are particularly suited for the production of oxygenated and hydrocarbon products that have at least one carbon-to-carbon bond in their structure. With the exception of ruthenium, all practical synthesis catalysts contain chemical and structural promoters. These promoters include copper, chromia, alumina and alkali. Alkali is of particular importance with iron catalysts, since it greatly enhances the conversion efficiency of the iron catalyst. Supports such as kieselguhr sometimes act beneficially.

The catalyzed reduction of carbon monoxide or carbon dioxide by hydrogen produces various oxygenated and hydrocarbon products, depending on the particular catalyst and reaction conditions chosen. The products that are formed include methanol, dimethyl ether, acetone, acetic acid, normal propyl alcohol, higher alcohols, methane, gaseous, liquid, and solid olefins and paraffins. It should be noted that this spectrum of products consists of aliphatic compounds; aromatic hydrocarbons either are totally absent or are formed in minor quantities.

In general, when operating at the lower end of the temperature range, i.e. from about 300° to about 500° F, in the reduction of carbon monoxide, and with pressures greater than about 20 atmospheres, thermodynamic considerations suggest that aliphatic hydrocarbons are likely to form in preference to their aromatic counterparts. Furthermore, in some catalytic systems it has been noted that aromatic hydrocarbon impurities in the synthesis gas inactivate the synthesis catalyst, and one may speculate that a number of known synthesis catalysts intrinsically are not capable of producing aromatic hydrocarbons.

The wide range of catalysts and catalyst modifications disclosed in the art and an equally wide range of conversion conditions for the reduction of carbon monoxide by hydrogen provide considerable flexibility toward obtaining selected products. Nonetheless, the spite of this flexibility, it has not proved possible to make such selections so as to produce liquid hydrocarbons in the gasoline boiling range which contain highly branched paraffins and substantial quantities of aromatic hydrocarbons, both of which are required for high quality gasoline. A review of the status of this art is given in "Carbon Monoxide-Hydrogen Reactions," Encyclopedia of Chemical Technology, Edited By Kirk-Othmer, 2nd Edition, Volume 4, pp. 446–488, Interscience Publishers, New York, N.Y., the text of which is incorporated herein by reference.

Oxygenated compounds and hydrocarbons are produced in varying proportions in the conversion of synthesis gas. This is understandable if, as proposed by some researchers in the field, the hydrocarbons arise via oxygenated intermediates such as alcohols. By selection of less active catalysts such as zinc oxide, it is possible to obtain oxygenated compounds as the major product. One particular commercial conversion is used to produce methanol from synthesis gas with substantially no coproduction of hydrocarbons. Suitable catalysts are those comprising zinc oxide, in admixture with promoters. Copper or copper oxide may be included in the catalyst composition. Particularly suitable are oxide catalysts of the zinc-copper-alumina type. Compositions of the type described are those currently used in commercial methanol synthesis. Contact of the synthesis gas with the methanol synthesis catalyst is conducted under pressure of about 25 to 600 atmospheres, preferably about 50 to 400 atmospheres, and at a temperature of about 400° to 750° F. The preferred gas space velocity is within the range of about 1,000 to 50,000 volume hourly space velocity measured at standard temperature and pressure. It is noted that the conversion per pass is from about 10% of the carbon monoxide fed to about 30%, i.e. in this process the unconverted synthesis gas must be separated from the methanol product and recycled.

Crystalline aluminosilicate zeolites have been contacted with methanol under catalytic conversion conditions. U.S. Pat. No. 3,036,134 shows a 98.4% conversion of methanol to dimethyl ether over sodium X zeolite at 260° C; 1.6 mole % of the product is a mixture of olefins through pentene, with butene the predominant product. Conversion of methanol over rare earth exchanged and zinc exchanged X zeolite has been reported to produce some hexanes and lighter hydrocarbons (see Advances in Catalysis, Vol. 18, p. 309, Academic Press, New York, 1968). It has recently been discovered that alcohols, ethers, carbonyl and their analogous compounds may be converted to higher hydrocarbons, particularly high octane gasoline, by catalytic contact with a special type zeolite catalyst. This conversion is described in copending U.S. Pat. Applications, Ser. Nos. 387,224, 387,223, and 387,222 filed on Aug. 9, 1973.

It is an object of the present invention to provide an improved method for converting fossil fuels high quality gasoline. It is a further object of this invention to provide a method for converting a mixture of gaseous carbon oxides with hydrogen to high quality gasoline. It is a further object of this invention to provide a novel method of converting synthesis gas to high octane gasoline. It is a further object of this invention to provide a process for the manufacture of substantially sulfur-free liquid hydrocarbon fuels. Further objects of this invention will be apparent to those skilled in the art.

BRIEF SUMMARY OF THE INVENTION

In accordance with the stated objects, one aspect of this invention provides a process comprising the following steps: coal or other fossil fuel is gasified to form synthesis gas; the gas is adjusted by one of several means to provide a volumetric ratio of hydrogen to carbon monoxide plus carbon dioxide of from 1.0 to 6.0; the adjusted synthesis gas is contacted with a carbon monoxide reduction catalyst in a first reaction zone to produce a reduction product comprising at least 20 weight percent oxygenated products; and, the reduction product is catalytically converted by contact with a catalyst which is a crystalline aluminosilicate zeolite having a silica to alumina ratio of at least about 12, a constraint index of about 1 to 12 and a crystal density, in the hydrogen form, of not substantially below about 1.6 grams per cubic centimeter in a second reaction zone to form a major fraction of aromatics-rich high octane gasoline and a minor fraction of useful products that include a hydrogen-rich gaseous mixture that may be recycled to the fossil fuels gasifier.

DETAILED DESCRIPTION AND PREFERRED EMBODIMENTS

The drawing of FIG. 1 will now be used to illustrate this invention in certain of its aspects, without being limited thereto. Coal, shale oil, or residua, or a combination thereof, is conveyed via line 1, 2 and 3, resp. and thence via line 4 to the synthesis gas plant, 5, where it is converted to synthesis gas. If hydrogen sulfide is produced in this plant, it may be separated and sent via line 6 to a treatment plant (not shown) for sulfur recovery. Synthesis gas, previously treated in a catalytic carbon monoxide shift converter and then reduced in carbon dioxide content by selective sorption, is conveyed via line 7 to a first reaction zone 8, where it is at least partially converted catalytically to produce a carbon monoxide reduction product that contains at least 20% by weight of oxygenated products. Part or all of the unconverted synthesis gas may be separated from such reduction product and recycled via line 10, but it is preferred to convey the total mixture via line 9 to the second reaction zone 11 where catalytic conversion to hydrocarbons and steam occurs. The reaction products from the second reaction zone 11 are conveyed via line 12 to a cooler, 13, and the cooled products are then conveyed via line 14 to a separator 15; note that the cooler 13 and line 14 and separator 15 may be one integral unit. Water is removed from separator 15 via line 16, gases via line 17, and liquid hydrocarbon products via line 18. The liquid hydrocarbon products are conveyed via line 18 to a distillation tower 19. Propane and butanes (LPG) are recovered via line 20, and gasoline via line 21. The gases disengaged in the separator 15 are conveyed via line 17 to storage 22, and recycled via lines 23 and 25 to the synthesis gas plant, or via lines 23 and 24 and line 7 to the carbon oxides converter 8.

Fossil fuel, as the term is used in this invention, is intended to include anthracite and bituminous coal, lignite, crude petroleum, shale oil, oil from tar sands, natural gas, as well as fuels derived from physical separation, or more profound transformations, of these materials, including coked coal, petroleum coke, gas oil, residua from petroleum distillation, and two or more of any of the foregoing materials in combination. It is an attribute of this invention that fuels which usually contain ecologically undesirable levels of sulfur, i.e. greater than 2% organically bound sulfur, may be used to produce products substantially free of sulfur. Organically bound sulfur, as distinguished from hydrogen sulfide, for example, is sulfur which is chemically bonded to one or more carbon atoms, and such sulfur is ordinarily difficult to remove from fossil fuels. Particularly preferred for the practice of this invention is to use coal. Non-fossil carbonaceous fuels also may be used, however; these include wood, cellulosic materials, organic animal waste, and any other organic matter characterized by significant fuel value.

Any of the described fuels may be converted to synthesis gas by techniques which are known in the art, and which are not regarded as constituting this invention. It is also contemplated to include in gasification techniques in situ processes such as the underground partial combustion of coal and petroleum deposits. In any case, it is to be understood that the gasification art employed shall be selected so as to produce raw synthesis gas comprising a mixture of carbon monoxide, carbon dioxide and hydrogen as the principal constituents. Synthesis gas, as first produced, contains impurities, including hydrogen sulfide and volatile organically bound sulfur compounds, including carbonyl sulfide. This mixture shall be referred to as raw synthesis gas.

Raw synthesis gas is next treated to remove impurities. Iron and nickel carbonyls, if present, should be removed since they will adversely effect the long term behavior of the catalysts used in the subsequent conversions. This purification may be carried out, for example, by absorption on activated carbon. Particulates and hydrocarbon impurities may be removed by sorption processes well known in the art, if so desired. It is very important, however to remove a major portion of the sulfur which may be present as hydrogen sulfide, organically bound sulfur compounds or mixtures of these. The organically bound sulfur compounds may be decomposed, for example, over a mixture of alkali metal carbonate and sulfurized iron at elevated temperature; the hydrogen sulfide, either initially present in the raw synthesis gas, or formed by decomposition of the organically bound sulfur compounds, may be reduced in concentration and substantially removed by scrubbing under pressure with ethanolamines, for example. For the purpose of this invention, it is preferred to remove at least 90% of the sulfur present initially in the raw synthesis gas to form purified synthesis gas.

The purified synthesis gas consists essentially of a mixture of hydrogen gas, with gaseous carbon oxides including carbon monoxide and carbon dioxide. By way of illustration, a typical purified synthesis gas will have the composition, in volume percentages, as follows: hydrogen, 51; carbon monoxide, 40; carbon dioxide, 4; methane, 1; and nitrogen, 4. Depending on the particular fuel and the particular gasification process, the hydrogen to carbon oxides ratio may vary widely. It is preferred to adjust the hydrogen-to-carbon oxides volume ratio in the synthesis gas to from 1.0 to 6.0 prior to use in subsequent conversions. Should the purified synthesis gas be excessively rich in carbon oxides, it may be brought within the preferred range by the well known water gas shift reaction; on the other hand, should the synthesis gas be excessively rich in hydrogen, it may be adjusted into the preferred range by the addition of carbon dioxide or carbon monoxide. Purified synthesis gas adjusted to contain a volume ratio of hydrogen to carbon oxides of from 1.0 to 6.0 will be referred to as adjusted synthesis gas.

It is desirable that the adjusted synthesis gas contain not more than 20% inert nitrogen since the economic cost for subsequent conversions are increased by excess diluent. Low levels of nitrogen are easily achieved by supplying essentially pure oxygen gas, in the quantities required, in the fossil fuels gasification step.

It is an essential feature of this invention that the adjusted synthesis gas is catalytically converted to oxygenated compounds in a first reaction zone and the oxygenated compounds are catalytically converted to liquid gasoline boiling range hydrocarbons in a second reaction zone. A number of catalysts are known that will cause the carbon monoxide to be reduced by the hydrogen of the synthesis gas to form oxygenated compounds, liquid hydrocarbons, and mixtures of these in varying proportions, depending on the particular catalyst and reaction conditions.

It is a preferred embodiment of this invention to catalytically convert the adjusted synthesis gas in such a manner that substantially all of the reaction product from the first reaction zone is oxygenated product, and thus obtain maximum benefit from this invention. The conversion to methanol, to dimethyl ether, or to mixtures of these and other oxygenated compounds is illustrative of this preferred embodiment.

Conventional methanol synthesis techniques are well suited for the purpose of this invention. Contact of the adjusted synthesis gas with a methanol synthesis catalyst, preferably under about 50 to 400 atmospheres, at a temperature from about 400° to 750° F, and at a volume hourly space velocity of from about 1000 to 50,000 volumes, serves to induce conversion of from about 10% to about 30% of the carbon monoxide feed to oxygenates, mainly methanol. Methanol may be formed as the almost exclusive product of the reduction, or it may be contaminated by higher alcohols such as ethanol, propanol, and butanols. In either case, it is possible to pass the gaseous product mixture from the first reaction zone through a condenser, separate the crude oxygenated product (methanol), and recycle the unconverted synthesis gas to the first reaction zone. However, it is preferred to directly convey the mixture of reduction product and unconverted synthesis gas to the second reaction zone without separation since this provides economies in handling and, in addition, the conversion in the second reaction zone is not adversely affected by the presence of the unreacted synthesis gas.

It is to be emphasized that the conversion in the first reaction zone may employ catalysts and reaction conditions which lead to improved efficiencies of carbon monoxide conversion, notwithstanding that the mixture of oxygenated compounds formed may ordinarily be considered undesirable for ordinary methanol synthesis because it contains substantial or even major fractions of oxygenated compounds other than methanol. This is so because the other oxygenated compounds such as dimethyl ether, ethanol, propanol and butanol are converted in the second reaction zone with an efficiency at least equal to pure methanol.

Thus, in a preferred embodiment of the present invention, crude methanol from the first reaction zone is fed to the second reaction zone without separation of oxygenated impurities. In this preferred embodiment full advantage is taken of insensitivity of the second reaction zone to these impurities, and furthermore the methanol synthesis catalyst and reaction conditions in the first reaction zone may be suitably modified to most efficiently affect the reduction of carbon monoxide.

Although maximum benefit from this invention is achieved by catalytic conversion of adjusted synthesis gas in a first reaction zone under conditions such that substantially all of the carbon monoxide reduction product is oxygenated product, substantial benefits will accrue if at least 20 percent by weight of the reduction product consists of oxygenated compounds. Metallic catalysts of the iron, cobalt and nickel variety are suitable for such conversions. Iron promoted by alkali is especially useful. By way of example, pure iron, roasted in an oxygen atmosphere in the presence of added aluminum and potassium nitrates provides a composition that contains 97% $Fe_3O_4$, 2.4% $Al_2O_3$, and 0.6% $K_2O$ with trace amount of sulfur and carbon. This composition after reduction with hydrogen at about 850° F catalyzes the conversion of synthesis gas at from 360° F to 430° F, and at 20 Atm. pressure, such that 65% of the carbon monoxide is reduced to a mixture consisting of about one third by weight of hydrocarbons boiling in the range of 200° F to about 680° F, and about two thirds of oxygenated compounds, mostly alcohols, in the same boiling range. This conversion is given by way of illustration only; other catalysts and conversion conditions capable of producing at least 20 percent by weight oxygenated compounds in the reduction product will be evident to those skilled in the art.

It is a feature of this invention that it is not necessary to separate the oxygenated compounds from the liquid hydrocarbons, prior to further conversion, when the two are produced simultaneously in the first reaction zone. Although the hydrocarbons produced in the first reaction zone are likely to be linear paraffins and olefins and therefore undesirable components of high octane gasoline, it is a remarkable attribute of this invention that these hydrocarbons undergo conversion to highly branched paraffins and aromatics along with the alcohols when the mixture is converted in the second reaction zone. It is a preferred embodiment of this invention to contact the unresolved mixture of hydrocarbons and oxygenated compounds with the catalyst in the second reaction zone, thereby taking full advantage of the cooperative interaction of the two reaction zones to produce maximum high octane gasoline. However, the reduction product mixture may be separated from the unconverted synthesis gas before contact with the catalyst in the second reaction zone.

Small quantities of ammonia are sometimes produced in the first reaction zone. Although not essential to this invention, it is highly desirable to remove these from the product mixture prior to contact with the catalyst in the second reaction zone, thereby prolonging the effectiveness of that catalyst. This may be done by brief contact with a solid acidic adsorbent, such as acid-treated clay, for example.

An essential step in the present invention is the catalytic conversion of the oxygenated compounds to high octane gasoline in a second reaction zone in contact with a novel class of zeolite catalysts. This recently discovered novel class of zeolites has some unusual properties. These catalysts induce profound transformations of aliphatic hydrocarbons to aromatic hydrocarbons in commercially desirable yields. Although they have unusually low alumina contents, i.e. high silica to alumina ratios, they are very active even when the silica to alumina ratio exceeds 30. The activity is surprising since the alumina in the zeolite framework is believed responsible for catalytic activity. These catalysts retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity.

An important characteristic of the crystal structure of this class of zeolites is that it provides constrained access to, and egress from, this intracrystalline free space by virtue of having a pore dimension greater than about 5 Angstroms and pore windows of about a size such as would be provided by ten-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalyst useful in this invention posess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic form within the channels. Although catalysts with a silica to alumina ratio of at least 12 are useful, it is preferred to use catalysts having higher ratios of at least about 30. Such catalysts, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by eight membered rings of oxygen atoms, then access to molecules of larger cross-section than normal hexane is excluded and the zeolite is not of the desired type. Windows of ten-membered rings are preferred, although excessive puckering or pore blockage may render these catalysts ineffective. Twelve-membered rings do not generally appear to offer sufficient constraint to produce the advantageous conversions, although structures can be conceived, due to pore blockage or other cause, that may be operative.

Rather than attempt to judge from crystal structure whether or not a catalyst posesses the necessary constrained access, a simple determination of the "constraint index" may be made by passing continuously a mixture of equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F for at least 15 minutes. The catalyst is then flushed with helium and the temperature adjusted between 550° F and 950° F to given an overall conversion between 10% and 60%. The mixture of hydrocarbons is passed at 1 liquid hourly space velocity (i.e. 1 volume of hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those having a constraint index from 1.0 to 12.0, preferably 2.0 to 7.0

The class of zeolites defined herein include those of the ZSM-5 type and is exemplified by ZSM-5, ZSM-11, ZSM-12, ZSM-21, TEA mordenite and other similar materials. Recently issued U.S. Pat. No. 3,702,886 describing and claiming ZSM-5 is incorporating herein by reference.

ZSM-11 is more particularly described in U.S. Pat. No. 3,709,979, the entire contents of which are incorporated herein by reference.

ZSM-12 is more particularly described in West German Offenlagunschrifft 2,213,109, the entire contents of which are incorporated herein by reference.

ZSM-21 is more particularly described in U.S. Application, Ser. No. 358,192, filed May 7, 1973, the entire contents of which are incorporated herein by reference.

TEA mordenite is more particularly described in U.S. Application Ser. No. 130,442 filed Apr. 11, 1971, the entire contents of which are incorporated herein by reference.

The specific zeolites described, when prepared in the presence of organic cations, are catalytically inactive, possibly because the intracrystalline free space is occupied by organic cations from the forming solution. They may be activated by heating in an inert atmosphere at 1000° F for one hour, for example, followed by base exchange with ammonium salts followed by calcination at 1000° F in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F for from about 15 minutes to about 24 hours.

Natural zeolites may sometimes be converted to this type zeolite catalysts by various activation procedures and other treatments such as base exchange, steaming, alumina extraction and calcination, in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12, ZSM-21 and TEA mordenite, with ZSM-5 particularly preferred.

The catalysts of this invention may be in the hydrogen form or they may be base exchanged or impregnated to contain ammonium or a metal cation complement. It is desirable to calcine the catalyst after base exchange. The metal cations that may be present include any of the cations of the metals of Groups I through VIII of the periodic table. However, in the case of Group IA metals, the cation content should in no case be so large as to effectively inactivate the catalyst. For example, a completely sodium exchanged H-ZSM-5 is not operative in the present invention.

In a preferred aspect of this invention, the catalysts hereof are selected as those having a crystal density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred catalysts of this invention are those having a constraint index as defined over of about 1 to 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g. on page 11 of the article on Zeolite Structure by W. M. Meier. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, howeve, is important as the locus of catalytic activity.

Because the catalyst for the synthesis gas conversion is a hydrogenation catalyst, the aromatization catalyst is most preferably maintained in a separate reaction zone, where it functions well even in the presence of unconverted synthesis gas.

In the practice of this invention, the conversion in the second reaction zone is conducted at a temperature of about 500° 1000° F, preferably about 600° to 800° F, a pressure of subatmospheric to about 50 atmospheres, and at a liquid hourly space velocity of about 0.1 to 50 LHSV.

The conversion with this special, high silica to alumina ratio, catalyst produces a sulfur-free, high quality gasoline fraction boiling in the range about 82° to 415° F which has a research octane number of at least about 80 without the addition of lead. A minor fraction of valuable liquefiable petroleum gas (e.g. propane) and a little dry gas (e.g. ethane and methane) also are produced. If severe reaction conditions are selected, the major fraction of the gasoline is aromatic hydrocarbons, and the paraffins are mostly branched. Thus, this total mixture may be separated into a small fraction suitably about 1%, of "dry gas" comprising methane, ethane, and ethylene, a small fraction, suitably about 26%, of liquefiable petroleum gas comprising propane and butanes, and a major fraction, suitably the remainder of about 73%, of gasoline with a research octane number of at least about 100 without requiring the addition of lead.

The liquefiable petroleum gas may be sold as a sulfur-free fuel, or it may be recycled to the gasification plant. In the latter case it need not be first separated from the "dry gas" fraction. The dry gas fraction may be burned as fuel or sold as such but preferably it is recycled to the fossil fuel gasification operation. Hydrogen is sometimes produced in the second, or aromatization, reaction zone. This hydrogen is a valuable recycle product which can be most useful in carbon oxide hydrogenation.

It will be seen by a consideration of this entire process that the individual steps are quite interrelated and mesh very nicely with each other through thermal and/or material conservation and recycle. The aromatization reaction is quite exothermic and its heat is most useful to generate steam used in other parts of the process.

What is claimed is:

1. In the process for manufacture of liquid hydrocarbon fuels boiling in the gasoline boiling range from coal which comprises converting the coal to a gaseous mixture of hydrogen and carbon oxides and converting said gaseous mixture to normally liquid hydrocarbons and oxygen-substituted hydrocarbons comprising methanol; the improvement comprising the additional step of contacting at least said oxygen-substituted hydrocarbons including said methanol with a catalytically active aluminosilicate zeolite having a silica to alumina ratio of at least about 12, a constraint index of about 1 to 12 and a crystal density, in the hydrogen form, of not substantially below about 1.6 grams per cubic centimeter at a temperature of about 500° to 1000° F, a space velocity of about 0.1 to 50 liquid hourly space velocity, and a pressure of about 1 to 50 atmospheres; and, covering liquid hydrocarbons.

2. A process as claimed in claim 1 wherein said catalyst is H-ZSM-5.

3. A process as claimed in claim 1 wherein the methanolsynthesis catalyst comprises zinc oxide and said crystalline aluminosilicate catalyst is H-ZSM-5.

4. A process as claimed in claim 1 wherein unconverted synthesis gas is segregated from said first reaction zone effluent stream prior to contacting the remainder of said stream with said catalyst in said second reaction zone.

* * * * *